United States Patent
Knappe et al.

(10) Patent No.: US 6,455,001 B1
(45) Date of Patent: Sep. 24, 2002

(54) FUNCTIONAL LAYERS OF HIGH PRECISION, PROCESS FOR THEIR PRODUCTION AND TEST STRIPS CONTAINING THESE FUNCTIONAL LAYERS

(75) Inventors: Wolfgang-Reinhold Knappe, Ludwigshafen (DE); Dan Mosoiu, Limburgerhof (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/426,939

(22) Filed: Oct. 22, 1999

(30) Foreign Application Priority Data

Oct. 23, 1998 (DE) .......................................... 198 49 000

(51) Int. Cl.⁷ .......................... G01N 21/00; G01N 31/22
(52) U.S. Cl. .......................................... 422/56; 422/58
(58) Field of Search ................................ 430/518, 539, 430/635; 106/154; 436/170; 422/56, 58

(56) References Cited

U.S. PATENT DOCUMENTS

| 4,312,834 A | | 1/1982 | Vogel et al. .................. 422/56 |
| 4,370,412 A | * | 1/1983 | Cruikshank et al. ......... 430/635 |
| 4,732,849 A | | 3/1988 | Seshimoto et al. .............. 5/12 |
| 5,536,470 A | | 7/1996 | Frey et al. ..................... 422/56 |
| 5,695,947 A | | 12/1997 | Guo et al. ..................... 435/11 |
| 5,846,837 A | | 12/1998 | Thym et al. ................. 436/170 |

FOREIGN PATENT DOCUMENTS

| DE | 2409068 A1 | 9/1975 | ............ G03C/1/48 |
| DE | 2752352 A1 | 6/1978 | ......... G01N/31/22 |
| DE | 3042857 A1 | 5/1981 | ............ C12Q/1/58 |
| EP | 0016387 B1 | 10/1980 | ......... G01N/33/52 |
| EP | 0582503 A1 | 2/1994 | ............ A61K/7/00 |
| EP | 0653637 A2 | 2/1994 | ......... G01N/33/52 |
| EP | 0690306 A1 | 1/1996 | ......... G01N/33/53 |
| EP | 0821233 A3 | 1/1998 | ......... G01N/33/52 |
| FR | 2730931 A1 | 8/1996 | ............ A61K/9/10 |
| WO | WO92/15879 | 9/1992 | ......... G01N/33/52 |
| WO | WO97/18036 | 5/1997 | ............ B01L/3/00 |

* cited by examiner

*Primary Examiner*—Jill Warden
*Assistant Examiner*—Samuel P Siefke
(74) *Attorney, Agent, or Firm*—Richard T. Knauer; Roche Diagnostics Corporation

(57) ABSTRACT

A skeleton-free functional layer of high precision which contains a wetting agent of formula I, II and/or III $$R^1\text{—CO—N}(R^2)\text{—CH}_2\text{—COOMe} \quad (I)$$

$$R^1\text{—CO—N}(R^2)\text{—CH}_2\text{—CH}_2\text{—SO}_3\text{Me} \quad (II)$$

$$HO_2C\text{—CH}_2\text{—CH}_2\text{—CH(NH—COR}^1)\text{—CO}_2\text{Me} \quad (III)$$

in which $R^1$ is a long-chained aliphatic residue, $R^2$ is an alkyl residue with 1 to 8 C atoms and Me represents hydrogen or a metal atom, a diagnostic test strip having this functional layer as well as processes for the production of these objects are described.

13 Claims, 2 Drawing Sheets

FUNCTIONAL LAYERS OF HIGH PRECISION, PROCESS FOR THEIR PRODUCTION AND TEST STRIPS CONTAINING THESE FUNCTIONAL LAYERS

The present invention concerns functional layers of high precision and their production, the use of N-acyl-N-alkyl-glycinates, N-acyl-taurates and/or N-acyl-glutamates to produce these functional layers as well as test strips and in particular diagnostic test strips which carry at least one functional layer of high precision according to the invention in their test elements.

So-called carrier-bound tests are often used for the qualitative or quantitative analytical determination of components of body fluids in particular of blood. In these the reagents are present on or in corresponding layers of a solid test carrier which is contacted with the sample. The reaction of liquid sample and reagents leads to a detectable signal especially to a change in colour which can be evaluated visually or with the aid of an instrument, usually by reflection photometry.

Test carriers are frequently in the form of test strips which are essentially composed of an oblong support layer made of plastic material and detection layers mounted thereon as test fields. However, test carriers are also known which are designed as small quadratic or rectangular plates. In the following description the term "test strips" is also intended to encompass test carriers which do not have a strip shape.

Test carriers of the above-mentioned type are for example known from the German Patent document 21 18 455. This describes diagnostic test carriers for the detection of analytes in liquids which are composed of a support layer and at least one detection layer containing the detection reagents. That surface of the detection layer that does not adjoin the support layer is provided with a cover layer. The cover layer can be composed of a fine-meshed network in the form of a fabric, knitted fabric or fleece. Plastic fabrics are stated as preferred networks in order to achieve a rapid wetting of the detection layer with sample liquid and to avoid interfering chromatographic effects. In order to detect an analyte in a liquid, such a diagnostic test carrier is dipped into a corresponding liquid, preferably urine. In this manner the detection layer comes into contact with a very large excess of liquid which cannot be taken up by the test carrier. However, depending on the duration of contact of the detection layer with the liquid to be examined different colour intensities can be observed.

As a rule the results obtained are more positive the longer the contact time is. Therefore a correct quantitative analyte determination is not possible in this manner when there is a large excess of sample.

On the other hand a sample volume that is too small for a test carrier construction is a frequent cause for false measured values in diabetes monitoring i.e. the regular control of the blood of diabetics for the content of glucose.

Test carriers which require as little volume as possible are therefore the goal of diverse current developments. However, such test carriers do not only have to yield correct measured values with very small sample volumes of about 3 $\mu$l, but they must also reliably operate with relatively large sample volumes of about 15–20 $\mu$l and must hold the sample liquid. Hygienic problems could occur if the liquid runs out of the test carrier for example if potentially infectious foreign blood is measured or if the test carrier is measured with an apparatus when there is a risk of contaminating the measuring instrument.

Test strips are known from DE-A-3042857 which have a sample distribution layer (spreading layer) on their analytical elements which has the function of uniformly distributing sample liquid applied as a spot over the entire test element. This spreading layer is composed of a cloth or a foam layer which is hydrophilized by impregnation with a wetting agent and is either pressed onto the upper gelatin layer of the analytical element which is still wet or is attached thereto by means of an additional adhesive layer.

The analytical elements of these known test strips which are referred to synonymously in the literature and in the following description as test elements, test fields, detection elements, detection fields or as detection layers have two or more layers which contain the reagents necessary to detect and quantitatively determine the analyte (in this case urea) or auxiliary substances such as radiation-absorbing substances. Such layers are referred to as functional layers in the following.

Diagnostic test carriers in the form of test strips which offer a considerable advance with regard to reproducibility of the test results even when different sample volumes are applied and with regard to hygienic handling are known from EP-A-0 821 233.

They contain a support layer with a detection layer arranged thereon having one or several functional layers which contain reagents required to determine the analyte in a liquid sample and a hydrophilic, but not capillary-active, relatively coarse-meshed overlay made of a network covering the detection layer which is larger than the detection layer and is attached to the support layer on both sides of the detection layer but in contrast rests directly on the detection layer without attachment i.e. essentially is in contact with the whole surface of this without a gap.

This network rapidly passes sample liquid applied to its surface onto the underlying detection layer and leads, with the aid of a foil layer that covers the boundary regions of the network, a sample excess which may be present into the boundary regions of the network which extend beyond the detection layer. In this manner small amounts of sample are made completely available to the detection layer but false-positive results are avoided.

Developments in the prior art apparently have the aim of achieving quantitative determinations of the analytes of interest that are as accurate as possible using test strips with smaller and smaller sample volumes. The improvement of the test strip construction also goes hand in hand with a reduction of the detection areas used for the analysis. Thus for example in a known instrument that is frequently used for the routine determination of blood sugar, the GLU-COTREND® instrument, only an area of ca. 1 mm diameter of the detection layer is evaluated.

An advantage of this trend is that small amounts of sample result in readily detectable colour signals on the small areas, but there is a risk that even slight local differences in the structure of the functional or detection layers can lead to serious measuring errors.

Conventional functional layers can contain a skeleton of a fibrous or non-fibrous porous material which incorporates the reagents required to detect the analytes and auxiliary substances and additives.

It is basically necessary to use those materials for the functional layers which are able to take up the liquid to be examined together with the components contained therein. These are so-called absorbent materials such as fleeces, fabrics, knitted fabrics, membranes or other porous plastic materials which can be used as a skeleton for the layer and of course decisively determine the structure and dimensions of the layer. The materials that come into consideration for the detection layer must of course also be able to carry reagents which are required to detect the analyte to be determined. In the simplest case all reagents required to detect the analyte are located on or in such a skeleton material.

Skeleton materials that are frequently used for the functional layer are papers, the above-mentioned textile fabrics made of natural or synthetic fibres or porous plastic materials such as membranes and in particular asymmetric porous membranes in which case the sample liquid to be examined is usually applied to the large-pored side of the membrane and the analyte is determined on the fine-pored side of the membrane. Particularly preferred porous membrane materials are polyamide, polyvinylidene difluoride, polyethersulfone or polysulfone membranes, in particular polyamide 66 membranes and hydrophilized asymmetric polysulfone membranes are used. The reagents for the determination of the analyte to be detected are usually incorporated into the aforementioned materials by impregnation or are applied to one side by coating. When coating asymmetric membranes it is preferable to coat the fine-pored side.

By nature the skeleton materials introduce an inhomogeneity in the layers which is averaged out when the colour signals generated by the analytes are evaluated over a large area but can interfere as the areas that are evaluated become smaller.

Hence various approaches have been made to generate skeleton-free functional layers of high precision i.e. with the fewest and smallest possible local inhomogeneities.

In this connection it is important that the layers flow well and adhere well to the bases. The aim is that the surface tension of the layer materials should be reduced or should approximate each other. For this the addition of organic solvents such as 1-hexanol or of wetting agents has been proposed. Another approach is to treat the surface of the respective base on which the layer is to be applied by plasma discharge (corona treatment). A combination of these measures is also possible.

However, these measures of the prior art have considerable disadvantages. Organic solvents such as 1-hexanol cannot be used in high concentrations since they are poorly soluble in water which is the preferred liquid phase for coating compounds. Water-miscible solvents such as acetone also lower the surface tension of the coating compounds but can only be used to a limited extent since they solubilize the plastic foils used as a base for the first layer which bends them and also bends the functional layers that are obtained. Such layers cannot be correctly processed and measured.

Wetting agents cannot be generally used and there is a special limitation when producing glucose detection layers since they must neither denature the enzyme glucose-dye-oxidoreductase (Gluc-DOR) that is used nor should they lyse the erythrocytes in the applied blood sample since otherwise the red colour of the measuring side of the detection layer of the test strips would considerably hinder the detectability and measurability of the colour signal of the detection reaction.

Corona treatments of the bases are primarily an additional process step and moreover require a corresponding expensive apparatus which represents a trouble-prone part of the production line.

There is thus still an urgent need to be able to produce skeleton-free functional layers of high precision i.e. those which have no or the fewest and smallest possible local irregularities.

The present invention addresses this requirement.

This invention concerns a skeleton-free functional layer of high precision comprising a film composed of a natural or synthetic film-forming polymer (film former), one or several compounds enabling the function of the layer, optionally auxiliary substances and/or additives which is characterized in that the layer contains wetting agents of formula I, II and/or III $$R^1\text{—CO—N}(R^2)\text{—CH}_2\text{—COOMe} \qquad (I)$$

$$R^1\text{—CO—N}(R^2)\text{—CH}_2\text{—CH}_2\text{—SO}_3\text{Me} \qquad (II)$$

$$HO_2C\text{—CH}_2\text{—CH}_2\text{—CH(NH—COR}^1)\text{—CO}_2\text{Me} \qquad (III)$$

in which $R^1$ is a preferably straight-chained or slightly branched aliphatic residue with 9 to 23 C atoms, in particular with 11 to 19 C atoms which is saturated or has one to three double bonds, $R^2$ is a preferably straight-chained or a slightly branched alkyl residue with 1 to 8, preferably 1 to 4 C atoms and Me represents hydrogen or a metal atom.

$R^1$ is preferably the aliphatic chain of lauric acid, myristic acid, palmitic acid, stearic acid, palmitoleic acid, oleic acid, linoleic acid, linolenic acid or isomers thereof and $R^2$ is methyl or ethyl.

Compounds of formulae I, II and III are of particular economic importance and of very good efficacy in which $R^1$ represents a quantity of alkyl residues in which the structure and proportion of the individual alkyl residues in the mixture corresponds to the structure and abundance in natural fats.

Compounds of formulae I, II and III are particularly preferred in which $R^1$—CO is an oleoyl, cocoyl or tallow fatty acid residue and $R^2$ is methyl.

The metal atom representing Me is expediently selected such that the compounds of formulae I, II and III are water-soluble. Me preferably denotes an alkali metal atom and in particular a sodium or potassium atom.

Skeleton-free functional layers according to the invention can contain a mixture of compounds of formulae I, II and/or III as a wetting agent.

For economic reasons skeleton-free functional layers according to the invention are particularly preferred which contain commercial products of formula I or II. Very suitable commercial products are for example sodium N-oleoyl-sarcosinate, which is readily obtainable from N-oleoyl-sarcosine (e.g. ®Crodasinic O from the Croda Company, Nettetal, Germany) and NaOH and sodium N-methyl-N-oleoyl-taurate (e.g. ®Geropon T 77 from the Rhone-Poulenc Chimie Company, Paris, France) and monosodium N-cocoyl-L-glutamate (e.g. ®Aminosoft CS-11 from the Ajinomoto Company, Tokyo, Japan).

It is very surprising that the high precision of the functional layers according to the invention is already achieved when they contain a total of 0.0075 to 2.5% by weight, preferably 0.01 to 2.0% by weight, in particular 0.03 to 1.0% by weight of the wetting agents of formulae I, II and/or III.

The high precision of the functional layers according to the invention results in a considerable increase in the accuracy of qualitative and quantitative determinations of analytes when these are incorporated into test strips as detection layers. Coating compounds according to the invention containing compounds of formulae I, II and/or III also have a considerably lower viscosity than coating compounds of the same composition but without compounds I, II or III and in many cases the extent of the decrease in viscosity is all the larger the higher the viscosity of the coating compound before the addition of compounds I, II or III. This results in a reduction in the differences in viscosity between coating compounds of different compositions so that the viscosity-dependent processing properties of various compositions are equalized which is a major advantage for example for the mechanical pouring of the layers.

It is observed visually that coating compositions according to the invention ☐xhibit a mirror-like surface shortly after their application and before drying. Hence they flow and spread very well on the support foil or on the already present first (dry) layer. The surface of layers without addition of compounds I, II or III appears visually to be considerably more uneven.

The functional layers according to the invention are preferably used as detection layers or are a component of detection layers in test strips especially diagnostic test strips and contain as such reagents or auxiliary substances and/or additives for the qualitative detection or quantitative determination of analytes in addition to the film formers.

Details of the composition of the functional layers according to the invention are as follows:

The functional layers are produced from dispersions or emulsions of polymeric film formers. Dispersion film formers contain microscopic polymer particles which are insoluble in the carrier liquid (usually water) which are dispersed in a fine dispersion in the carrier liquid. If the liquid is removed by evaporation during film formation then the particles approach each other and finally touch. The large forces which occur in this process and a reduction of the surface energy associated with the film formation result in a growth of the particles to a largely continuous film layer. Alternatively it is also possible to use an emulsion of the film former in which it is dissolved in a solvent. The dissolved polymer is emulsified in a carrier liquid which is imiscible with the solvent.

Polyvinyl esters, polyvinyl acetates, polyacrylic esters, polymethacrylic acid, polyvinylamides, polyamides and polystyrene are suitable as polymers for such film formers. Mixed polymers e.g. of butadiene, styrene or maleic acid ester are also suitable in addition to homopolymers.

If a functional layer according to the invention is combined with an additional inventive or also non-inventive functional layer to form a detection layer then the functional layers can be produced from coating compositions which contain the same polymeric film former or they can be produced from coating compositions which contain different polymeric film Formers.

However, so-called open films also come into consideration for the functional layer as described for example in EP-B-0 016 387. For this solids in the form of fine insoluble organic or inorganic particles are added to an aqueous dispersion of film forming organic plastics and the reagents required for the detection reaction are additionally added. Suitable film formers are preferably organic plastics such as polyvinyl esters, polyvinyl acetates, polyacrylic esters, polymethacrylic acid, polyacrylamides, polyamides, polystyrene, mixed polymers for example of butadiene and styrene or of maleic acid ester and vinyl acetate or other film forming natural and synthetic organic polymers as well as mixtures of the same in the form of aqueous dispersions. The dispersions can be spread on a base to form a uniform layer which results in a water-resistant film after drying. The dry films have a thickness of 10 $\mu$m to 500 $\mu$m, preferably of 30 to 200 $\mu$m. The film can be used together with the base as a support or it can be mounted on another support for the detection reaction. Although the reagents required for the detection reaction are normally added to the dispersion used to produce the open films, it may also be advantageous to impregnate the final film with the reagents after its production. It is also possible to preimpregnate the filling materials with the reagents.

An additional example of a preferred detection layer according to the invention is a film layer as described in WO-A-92 15 879. This layer is produced from a dispersion or emulsion of a polymeric film former which additionally contains a pigment, a swelling agent and the detection reagent in a homogeneous dispersion. Polyvinyl esters, polyvinyl acetates, polyacrylic esters, polymethacrylic acid, polyvinylamides, polyamides and polystyrene are particularly suitable as polymeric film formers. In addition to homopolymers mixed polymers e.g. of butadiene, styrene or maleic acid ester are also suitable. Titanium dioxide is a particularly suitable pigment for the film. The swelling agent used should have particularly good swelling properties and methyl vinyl ether maleic acid copolymer is particularly recommended.

In addition to the film formers and the reagents for the analyte detection, auxiliary substances and/or additives are very important as a component of the functional layers according to the invention. They serve to adapt the layers to special requirements for example to improve the detectability of the colour reaction, stabilize the reagent systems and/or to prepare the sample liquid by a filter action, e.g. by separating certain components which would interfere with the detection. Examples of such additives are pigments with selected refractive indices, swelling agents or non-porous or porous fillers such as kieselgur (diatomaceous earth).

By adding a good swelling agent (i.e. a substance which increases its volume by uptake of water) one not only obtains layers which are relatively rapidly penetrated by sample liquid but which, despite this opening effect of the swelling agent, have good erythrocyte and additionally also blood pigment separation properties. The swelling properties should be so good that for a test for which the rate of colour formation—such as for example a glucose detection reaction—largely depends on the penetration of the sample liquid through the layer, the optically detectable reaction is measurable after a maximum of one minute. Xanthan gum and methyl vinyl ether maleic acid copolymers have proven to be particularly suitable swelling agents.

Reagent systems for the detection of particular analytes by colour formation are known to a person skilled in the art. It is possible that all components of the reagent system are located in one film layer. It is, however, also possible that the components of the reagent system are divided between the two film layers. Advantageously the colour forming reagent system is at least partly located in the first film layer.

Colour formation is understood in the scope of the present invention not only to mean the Transition from white to coloured but also any colour change whereby of course those colour changes are particularly preferred which are associated with the largest possible shift of the maximum absorption wavelength ($\lambda$ max).

The layers according to the invention are produced on a support. This is advantageously a preferably transparent foil as a base support or a foil already provided with an inventive or non-inventive layer. Plastic foils come into particular consideration as the base support which are liquid impermeable. Polycarbonate foil has proven to be particularly preferred.

The thickness of the functional layers according to the invention is usually not more than 0.1 mm, preferably not more than 0.05 mm.

In addition to the skeleton-free functional layers of high precision according to the invention that are described above, the use of compounds of formula I and/or II in which the residues $R^1$, $R^2$, $R^3$ and Me have the meanings stated in claim 1 to produce skeleton-free functional layers of high precision is also a subject matter of the present invention.

The invention also concerns a process for the production of skeleton-free functional layers of high precision by coating a support with a liquid or paste-like coating composition composed of a liquid solvent or dispersant, a solution, a dispersion or a redisperseble or soluble preparation of a natural or synthetic film forming polymer (film former), one or several compounds enabling the function of the layer and optionally auxiliary substances and/or additives and subsequently removing the liquid solvent or dispersant, characterized in that the liquid or paste-like mixture contains a wetting agent of formulae I, II and/or III in which the residues $R^1$, $R^2$ and Me have the meanings stated above.

Solvents in the sense of this description of the process are also so-called apparent solutions i.e. systems of solvent and high-molecular substances which have no phase boundary but exhibit a Tyndall effect. The term dispersion is intended to include all systems composed of a continuous liquid phase, the dispersant and a discontinuous phase that is finally dispersed therein i.e. also emulsions. Suitable groups of natural and synthetic film formers have already been described above in connection with the description of the materials of the functional layers according to the invention.

The liquid or paste-like coating composition used in the process according to the invention contains a total of 0.0075 to 2.5% by weight, preferably 0.01 to 2.0% by weight, in particular 0.03 to 1.0% by weight relative to the weight of all components of the coating composition with the exception of water, of wetting agents of formulae I, II and/or III in which the residues $R^1$, $R^2$ and Me have the meanings stated above.

The support on which the layer according to the invention is generated can already carry one or several inventive or non-inventive functional layers.

The coating can be carried out by all known coating methods which enable a metered application of the coating composition in particular by pouring, by spreading using brushes, paint brushes or knife coating or by roller application or by combinations of these methods. Thus a layer applied by roller can be levelled by brushing or targetted streams of air (so-called air-brushing); blades of various known constructions can be used to remove a possible excess of applied coating composition.

If the support material or/and the other components of the coating composition do not impose other constraints, the liquid phase of the coating composition can be expediently removed at temperatures between room temperature and the boiling point of the liquid phase, preferably at temperatures of about 40 to 80° C.

The present invention additionally concerns test strips composed of a—as a rule flexible—flat-shaped carrier on which one or several test elements are arranged next to one another in a test region which each comprises one or several functional layers which rest on top of one another and optionally are covered by an overlay made of a spreading material which are characterized in that at least one of the functional layers is a skeleton-free functional layer of high precision according to the invention.

The test elements composed of one or several functional layers can, as already mentioned above, also be referred to as test fields, detection elements, detection fields or as detection layers.

These terms are also used synonymously in the following description.

With regard to work economy those test strips according to the invention which have two single-layer or multilayer test fields for the same or different analytes which directly adjoin one another or are separated by a gap are particularly advantageous.

If, as is preferred, the test strips are used for diagnostic purposes, then the test fields contain reagents in their functional layers for the detection of a diagnostically utilizable analyte.

The flat-shaped carrier (support layer) of the test strip according to the invention is advantageously composed of a material which does not take up the liquid to be examined. These are so-called non-absorbent materials of which plastic foils for example made of polystyrene, polyvinyl chloride, polyester, polycarbonate or polyamide are particularly preferred. However, it is also possible to impregnate absorbent materials such as wood, paper or cardboard with water-repellent agents or to coat them with a water-resistant film where silicone or hardened fats can be used as hydrophobizing agents and for example nitrocellulose or cellulose acetate can be used as film formers. Metal foils or glass are suitable as additional support materials.

Since the visual assessment and/or the apparative measurement of the test results which are usually in the form of colour changes of the detection layer usually takes place from the side of the detection element opposite to the sample application site, it is necessary that the test strip support is composed of a transparent material and/or has a hole in the region of the test field which is covered by the detection layer. The detection layer but at least the reaction zones of the detection layer are then visible through the perforation. However, several reaction zones of the detection layer may also be visible through one hole.

Especially in preferred test strips with two or several detection elements arranged next to one another, the perforation of a diagnostic test carrier according to the invention can also be composed of two or several holes of the same or different shape which can be used to determine analyte (one or several analytes). Various detection layers or only one detection layer with several reaction zones can be arranged above the holes so that through each hole one detection layer or one reaction zone can be observed.

In a preferred embodiment of the diagnostic test carrier according to the invention there is a hole in the support layer below a detection layer through which the detection layer or a reaction zone can be observed which has a somewhat smaller diameter than the smallest linear extension of the detection layer so that the detection layer rests on the support layer outside the hole and can be attached to the support layer by means of a thin adhesive tape. The detection layer is usually adequately attached by double-sided adhesive tapes arranged on both sides and by the spreading layer lying over the detection layer and its attachment to the support layer.

In order to be able to measure the test reaction simply but nevertheless reproducibly, the test strip support advantageously has adjustment marks e.g. notches or holes which engage in corresponding adjusting elements of the measuring instrument used e.g. a ®GLUCOTREND instrument and thus ensure a correct position of the test strip in the measuring instrument.

FIGS. 1 to 4 serve to illustrate this and the following embodiments.

Figure 1:
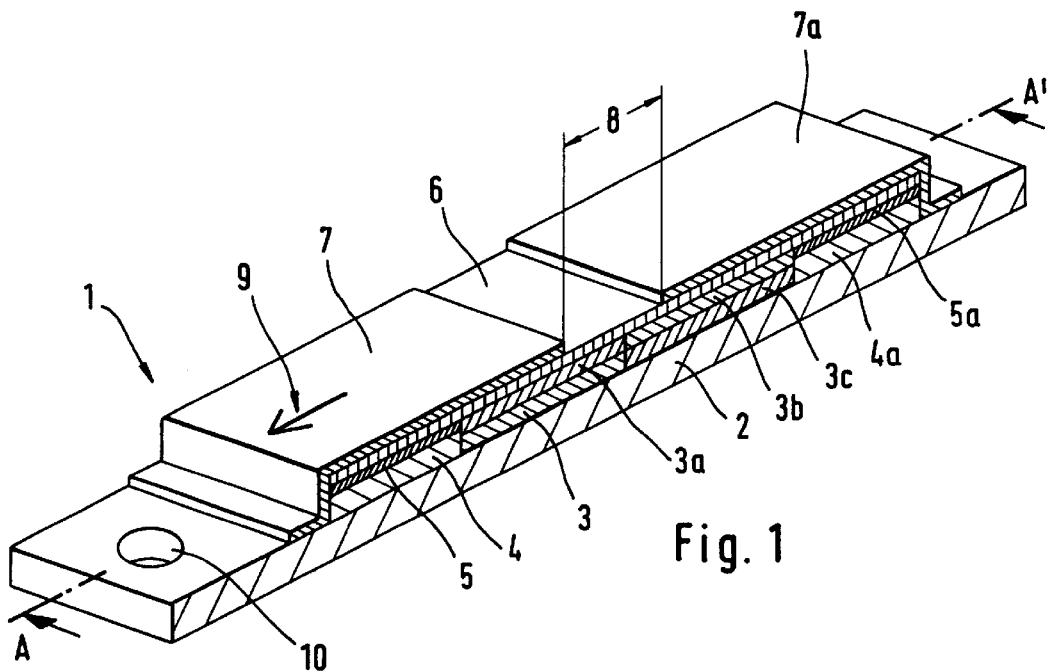
FIG. 1 shows a perspective top-view.

The reference numerals used in the figures have the following meaning:

| 1: | test strip |
|---|---|
| 2: | flexible carrier |
| 3 to 3c: | functional layers according to the invention |
| 4 and 4a: | spacers |
| 5 and 5a: | adhesion layers |
| 6: | spreading layer |
| 7 and 7a: | protective cover |
| 8: | application area for sample material |
| 9: | mark for the direction of insertion |
| 10: | positioning hole |
| 11 and 12: | observation and measurement openings |
| 13: | base foil layer |

Figure 2:
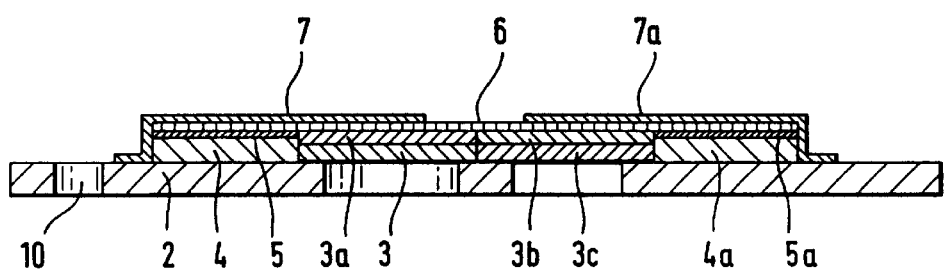
FIG. 2 shows a section along the cut line A–A'.
Figure 3:
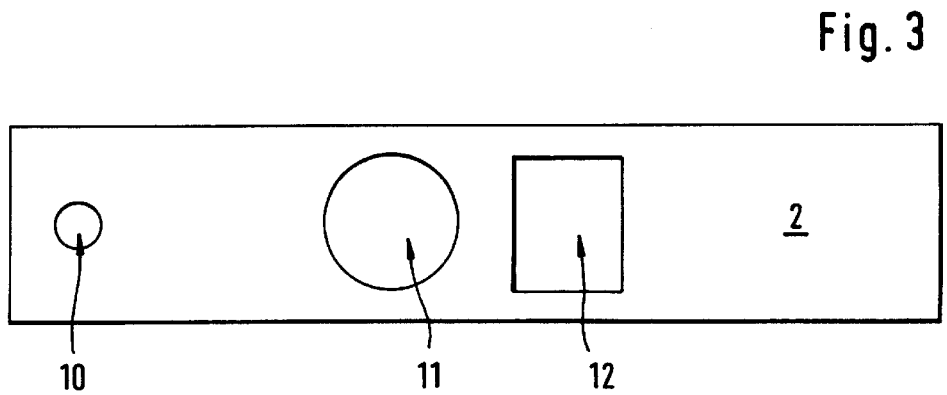
FIG. 3 shows a top-view of the underside of an embodiment of a test strip according to the invention.

FIG. 1 shows a perspective top-view, FIG. 2 shows a section along the cut line A–A', FIG. 3 shows a top-view of the underside of an embodiment f a test strip according to the invention with a detection area and a spreading layer according to the invention. This representation is not to scale in order to clearly illustrate the construction. A concrete dimensioning of this embodiment can be seen in the practical example 2.

The diagnostic test strip (1) according to the invention shown perspectively in FIG. 1, in section in FIG. 2 and from below in FIG. 3 has two detection layers on a support layer (2) which are each composed of two functional layers of high precision according to the invention (3 to 3c) that lie on top of one another and are covered by a spreading layer (6). The spreading overlay (6) is attached to the support layer (2) next to the detection layers by means of spacers (4, 4a) and adhesion layers (5, 5a). These spacers can in practice also be hot-melt adhesive areas or double-sided adhesive tapes which fix the spreading overlay (6) on the support layer (2). Ideally the spacers together with their adhesive surfaces have approximately the same thickness as the detection layer. The construction shown here additionally has covers (7, 7a) which are attached to the support layer (2) and to the spreading overlay (6). They are arranged in such a way that they cover the regions extending beyond the detection layers and a part of the area of the spreading overlay (6) resting on the detection layer. However, they leave an area in the middle of the detection layer free which represents the sample application site (8). The sample liquid to be examined is applied to this. There is a printed arrow (9) on the left cover (7) which shows the user which end of the test carrier (1) he should place or insert into a measuring instrument. The positioning hole (10) serves to hold the test strip, in the case of a measurement by an apparatus such as by reflection photometry, at an exactly predetermined position in the apparatus. This can for example be achieved in that for example a pin extends into the positioning hole (10) and in this manner fixes the test carrier (1) at a predetermined position.

The attachment of the detection layers and the spacers to the support which is of course present which can also be achieved by adhesion layers is not shown in the figures.

FIG. 3 shows the underside of the test strip according to the invention containing the positioning hole (10) placed in the support (2), the round observation opening (11) and the rectangular measurement opening (12) through which the detection layer can be inspected and measured.

Figure 4:
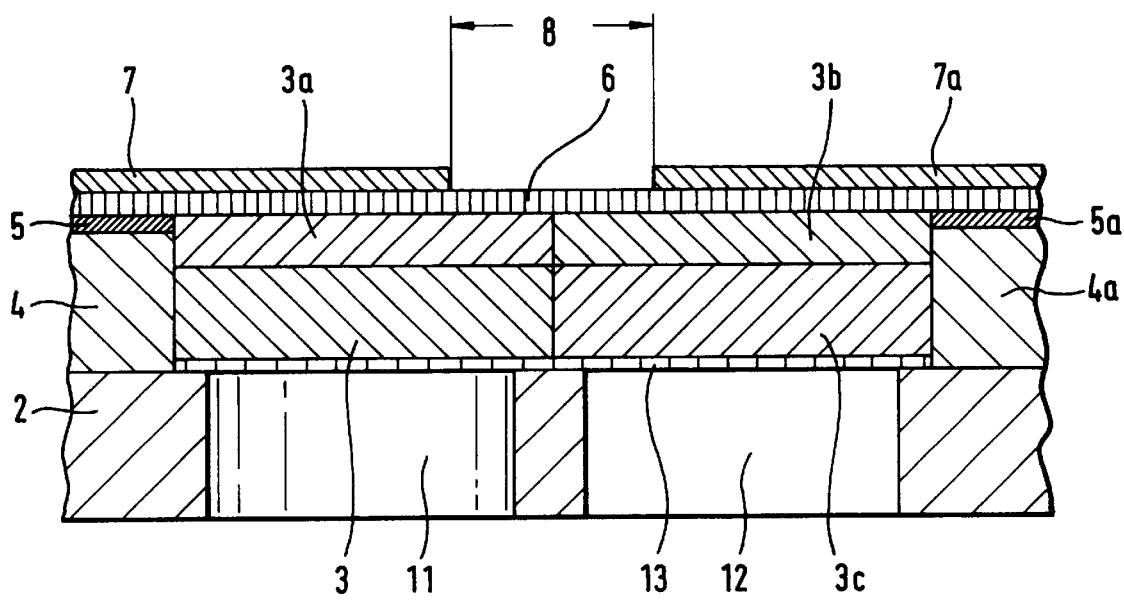
FIG. 4 shows an enlarged section from the section shown in FIG. 2.

For clarification FIG. 4 shows an enlarged section from FIG. 2. Two detection layers each composed of two superposed functional layers according to the invention of high precision (3 to 3c) and a base foil layer (13) carrying the functional layers are directly adjacent to one another on the support layer (2) and are covered by the spreading overlay (6). The spreading overlay (6) is attached to the support layer (2) next to the detection layers by means of spacers (4, 4a) and adhesion layers (5, 5a). In addition parts of the covers (7, 7a) which are attached to the spreading overlay (6) can be seen.

In order to manufacture a test element of a test carrier according to the invention firstly the functional layers required to construct the test element are generated on a support as described above. If the test element comprises two functional layers then these are produced successively from a homogeneous dispersion of the said components. For this the transparent foil is used as a base to shape the coating compound for the first film layer. After the coating compound for the first film layer has been applied with a certain layer thickness, the layer is dried. Afterwards the coating compound for the second layer is also applied in a thin coating layer and dried. After drying the thickness of the first and second film layer should be together no more than 0.2 mm, preferably no more than 0.12 mm and particularly preferably no more than 0.08 mm.

Detection elements with more than two functional layers can also be produced in an analogous manner.

In a test strip according to the invention it is not necessary that all functional layers are high precision layers according to the invention. On the contrary the layers can be layers which only have auxiliary functions or be conventional layers without containing compounds of formulae I, II and/or III. However, it is usually advantageous to produce all layers according to the invention in high precision.

The detection elements can be attached to the support material by methods known to a person skilled in the art from test carrier technology. For example the attachment can be by means of hot-melt adhesive or cold setting adhesive. Double-sided adhesive tapes have also proven to be advantageous.

The spreading overlay above the test element is not connected with it and only rests loosely on it, but the surface area is in contact with it. Normally the overlay if viewed in the direction of the longitudinal axis of the test strip is attached to the support in front of and behind the test field. It is advantageous when the means that are used to attach the overlay have about the same thickness as the detection layer(s). It then serves as a spacer in order to hold the overlay according to the invention on a continuous plane even outside the area of the detection layer(s).

The purpose of the spreading overlay is to uniformly and as rapidly as possible supply sample liquid to the detection element or optionally to distribute it uniformly over all detection elements that are present. Optionally the spreading overlay is used to conduct excess analyte sample away from the test element. In this manner the signal intensity when an analyte is present is independent of the amount and the duration of contact of the sample liquid with the detection layer. The colour which is usually developed after completion of the detection reaction within a few seconds to a few minutes thus remains unchanged for the measurement. It is only determined by the stability of the colour generating system but not for example by analyte which diffuses back from the excess liquid into the detection layer. False-positive results are also avoided and a quantitative analyte determination is enabled.

In order to fulfil this additional purpose the spreading layer is optionally larger than the test element to be covered so that a sample excess can be taken up by the parts of the overlay that "jut out" beyond the test element.

In addition it is important that the overlay is attached to the support layer in such a manner that a capillary-active liquid transport is possible from the detection layer into that part of the overlay which is attached to the support layer. The attachment can be by means of hot-setting or cold-setting adhesive. In this connection application of the adhesive as a spot or grid is advantageous since this facilitates the capillary-active transport of liquid particularly well. This capillary-active liquid transport must in particular be possible when the detection layer is saturated with liquid. Adhesive tapes containing natural or synthetic rubber have proven to be particularly suitable for the processing.

A spreading overlay which is very well suited for the combined purpose of distributing sample liquid rapidly and uniformly over the test element and conducting away excess sample liquid into lateral storage regions is composed for example of a slip-resistant fabric with a linen weave and a mesh size of 200 to 300 $\mu$m, preferably 250 to 300 $\mu$m made of monofilaments with a denier of 150 to 300 dtex, preferably 200 to 250 dtex.

Depending on the type of reaction to be carried out of the analyte to be detected, the construction of the test strip and the type of sample substance, the spreading material can be selected such that it either has a high permeability i.e. it conducts sample liquid particularly rapidly to the test field or its spreading action dominates in order for example to reliably distribute sample material over two or several adjacent test fields. In any case the permeability an spreading action are matched such that even with a high permeability, a sample excess can be reliably led away into the parts of the overlay which are no longer in contact with the test field(s).

A major advantage of a test carrier constructed in this manner is that it is not necessary to apply an exactly predetermined volume of a sample liquid to the test carrier but rather that a large range is available for the application volume. As already mentioned, excess liquid is conducted away from the detection layer by the spreading overlay protruding beyond the detection layer. Since excess liquid is led away from the detection layer, hygienic aspects are also taken into consideration. It reliably prevents liquid from dripping out of the test carrier or contact of liquid with for example parts of an instrument into which the test carrier is placed in order to be evaluated. This is a very important aspect especially when examining blood or samples derived from blood such as plasma or serum.

The reagents which are required to detect particular analytes and optional expedient auxiliary substances and/or additives can be combined in a single functional layer according to the invention.

However, cases are also conceivable where it may be more advantageous to distribute the reagents and auxiliary substances and/or additives that may have to be used over several absorbent or swellable material layers which are then arranged on top of one another, touching each other over their whole area and are preferably permanently joined together. The terms test element, test field, detection element and detection layer used should include those cases in which reagents are located only in or on one layer or in two or even several layers as described above.

In addition the detection elements can also contain a layer which is able to separate plasma or serum from whole blood such as a glass-fibre fleece as known for example from EP-B-0 045 476. One or several such separation layers can be located above one or several layers which carry the detection reagents. Such a construction should also be covered by the terms test element, test field, detection element and detection layer.

In a diagnostic test carrier according to the invention it is particularly preferable to use a test field as a detection layer which is composed of two functional layers. This test field comprises a transparent foil on which a first and a second functional layer are applied on top of each other in this order. It is essential that the first layer located on the transparent foil scatters light considerably less in a wet state than the overlying second layer. The non-coated side of the transparent foil is referred to as the detection side and the side of the second layer which is opposite to that side of the second layer which lies on top of the first is referred to as the sample application side.

The two functional layers can be produced as coating compositions which contain the same polymeric film former or they can be produced from coating compositions which contain different polymeric film formers.

If there are special test functions and/or test conditions such as in the determination of glucose in whole blood, it is expedient to form the layers such that, apart from a good erythrocyte separation, they also have optical features which facilitate the observation of the detection reaction and the exactness of the assessment and improve the instrument detection of the measurement.

For this the first layer expediently contains a swelling agent and optionally a weak light-scattering filling material, the second layer contains a swelling agent and at least one strongly light-scattering pigment. Since the weakly light-scattering filling materials and the strongly light-scattering pigments are of major importance for the optical properties of the film layers, the first and the second film layer contain different filling materials and pigments.

The first functional layer should either contain no fillers or fillers whose refractive index is close to the refractive index of water. Silicon dioxide, silicates and aluminium silicates have proven to be particularly suitable for this. A sodium aluminium silicate with the trade name Transpafill® (Degussa Company, Frankfurt (M), Germany) is particularly preferred.

The second layer should scatter light as strongly as possible. Ideally the refractive index of the pigments in the second film layer should be at least 2.5. Therefore titanium dioxide is preferably used. Particles with an average diameter of about 0.2 to 0.8 $\mu$m have proven to be particularly advantageous.

An inert cover made of sample-impermeable, usually water-impermeable and non-absorbent material can be arranged over the spreading overlay of the diagnostic test carrier according to the invention in such a manner that it covers the region of the spreading overlay outside the detection layer. Ideally the cover also extends into the region of the detection layer but, however, it in any case leaves a middle part of the overlay according to the invention which covers the detection layer free. This free part of the overlay is referred to as the sample application site. The space left free by the inert cover for sample application is expediently 2 to 5 mm. The sample application site is preferably located above the perforation in the support layer through which signal generation in the detection layer can be observed.

A sample application site can be accessed through a cover particularly simply by means of two strip-shaped plastic foils which leave a strip-like region of the spreading overlay covering the detection layer free. If 2 or more sample application sites are intended then three or more strip-shaped plastic foils have to be used. The foils used for the cover are attached to the overlay according to the invention and optionally to the support layer. Hot-melt adhesives which are preferably applied in spots or in a pattern on the support layer or on the underside of the cover are suitable for such an attachment or adhesive tapes if the foils are not self-adhesive. If it is intended to remove a sample excess that may be present then care must be taken that a capillary gap remains between the cover and the spreading overlay which can take up the excess sample liquid from a detection layer saturated with liquid.

In addition the cover also protects the excess liquid removed from the detection layer from outside contact and prevents this liquid from easily dropping from the test carrier.

Covering parts of the overlay according to the invention and thus marking the sample application site ensures that liquid can only reach the detection layer at the optimal site for this. In combination with a detection layer which only takes up a small amount of liquid and nevertheless ensures an intensive signal generation, it is ensured that reliable analyte determinations are possible even with very small sample volumes. Since the test carrier according to the invention is only composed of a few components which can be simply and rapidly assembled, it is very cheap to manufacture.

In order to carry out a method for the determination of an analyte in a liquid sample with the aid of a diagnostic test carrier according to the invention, sample liquid is applied to the side of the spreading overlay which faces away from the detection element and ideally sufficient so that the liquid which passes through the spreading overlay completely saturates the detection layer. Body fluids such as blood, plasma, serum, urine, saliva etc. come into particular consideration as the sample liquid. Blood or liquids derived from blood such as plasma or serum and urine are particularly preferred sample liquids. The spreading overlay leads excess liquid away from the detection element into the region of the overlay which protrudes beyond the detection element. Then if the analyte to be determined is present a signal can be detected in the detection layer. Such a signal is advantageously a colour change which is understood as colour formation, loss of colour as well as colour transition. In order to determine the analyte to be detected in the sample liquid, the detection element or at least the reaction zones i.e. the regions of the detection element which carry reagent and can be observed and measured for signal formation are visible in the diagnostic test carrier according to the invention through the support.

As already described above this can be achieved by the support layer being transparent or perforated below the detection element.

The intensity of the colour change is a measure for the amount of analyte in the examined liquid sample. It can be evaluated visually or quantitatively with the aid of an instrument, usually by reflection photometry, in which case calibration curves created in preliminary experiments can be used. Alternatively the content of analyte can be displayed directly by means of the instrument's software.

Those embodiments of the present invention are also particularly preferred which have a combination of several preferred features.

The following practical examples illustrate the production of functional layers and test strips according to the invention and show their significant superiority over conventional products.

EXAMPLE 1

The example illustrates coating compositions for the production of functional layers according to the invention and shows the effect of a wetting agent used according to the invention on the surface tension of the compositions.

Mixture A

The following components are added together in a beaker as pure substances or in the form of stock solutions in the following composition and mixed by stirring:

water: 820.0 g
sodium N-methyl-N-oleoyl-taurate*: X g
citric acid 1-hydrate: 2.5 g
calcium chloride 2-hydrate: 0.5 g
sodium hydroxide: 1.4 g
xanthan gum: 3.4 g
tetraethylammonium chloride: 2.0 g
N-octanoyl-N-methylglucamide: 2.1 g
polyvinylpyrrolidone (MW 25000): 3.5 g
Transpafill (sodium-aluminium silicate): 62.1 g
polyvinylpropionate dispersion (50% by weight in water): 60.8 g
Bis-(2-hydroxyethyl)-(4-hydroxyiminocyclohexa-2,5-dienylidine)-ammonium chloride: 1.2 g
2,18-phosphomolybdic acid hexasodium salt: 16.1 g pyrroloquinoline quinone: 32 mg
glucose dehydrogenase rec. from Acinetobacter calcoaceticus, 1.7 MU EC 1.1.99.17: (2.4 g)

* (Geropon® T77, commercial product from the Rhone-Poulenc Chimie Company)

The total composition is adjusted to a pH of about 6 with NaOH. The above mixture was prepared using the following amounts X of Geropon® T77:

X=0 corresponding to 0% by weight Geropon
X=0.0098 corresponding to 0.001% by weight Geropon
X=0.098 corresponding to 0.01% by weight Geropon
X=0.29 corresponding to 0.03% by weight Geropon
X=0.98 corresponding to 0.1% by weight Geropon
X=2.9 corresponding to 0.3% by weight Geropon The surface tension [mN/m] of each of the mixtures prepared in this manner was measured at 20° C. by the ring method according to DIN 53914 using a digital tensiometer K10T from the Krüss GmbH Company, Hamburg, Germany. The results of the measurements are shown in table 1.

Mixture B

The following components are added together in a beaker as pure substances or in the form of stock solutions in the following composition and mixed by stirring:

water: 579.7 g
sodium N-methyl-N-oleoyl-taurate: X g
sodium hydroxide: 3.4 g
Gantrez® (methyl vinyl ether maleic acid copolymer) 13.8 g
N-octanoyl-N-methylglucamide: 3.6 g
tetraethylammonium chloride: 9.7 g
polyvinylpyrrolidone (MW 25000): 20.2 g
titanium dioxide: 177.1 g
kieselguhr: 55.3 g
polyvinylpropionate dispersion (50% by weight in water): 70.6 g
2,18-phosphomolybdic acid hexasodium salt: 44.3 g
potassium hexacyanoferrate (III): 0.3 g This mixture was also prepared using the quantities of Geropon® stated for X. Subsequently surface tensions were measured as for mixture A and are shown in table 1.

TABLE 1

Surface tension of the coating compositions A and B in relation to the Geropon concentration.

| Geropon concentration [%] | Surface tension A | Surface tension B |
| --- | --- | --- |
| 0 | 48.1 | 58.1 |
| 0.001 | 46.2 | 56.4 |
| 0.01 | 43.8 | 50.7 |
| 0.03 | 41.7 | 41.5 |
| 0.1 | 40.4 | 39.3 |
| 0.3 | 38.5 | 39.3 |

EXAMPLE 2

Production of test strips according to the invention

A 5 mm wide double-sided adhesive tape polyester support and synthetic rubber adhesive) is mounted parallel on a strip-shaped 50 mm wide titanium dioxide-containing polyester support layer at a distance of 18.6 mm to its left edge (measured from the left edge of the adhesive tape). Two holes are punched out of this combination at a distance of 6 mm i.e. a positioning hole and an inspection and measuring hole whose centres lie on a straight line perpendicular to the longitudinal axis of the carrier strip. The first hole, the positioning hole, is circular, has a diameter of 2.6 mm and its centre is at a distance of 4 mm from the left edge of the support layer. The second hole is also round with a diameter of 4 mm. The centre of the second hole is at a distance of 21 mm from the left edge of the support layer.

Afterwards the protective paper of the double-sided adhesive tape is pulled off.

The procedure for the production of a detection layer which is composed of 2 film layers is as follows:

The following components are added together in a beaker as pure substances or in the form of stock solutions in the following composition and mixed by stirring:

Water: 820.0 g
sodium N-methyl-N-oleoyl-taurate: 0.29 g
citric acid 1-hydrate: 2.5 g
calcium chloride 2-hydrate: 0.5 g
sodium hydroxide: 1.4 g
xanthan gum: 3.4 g
tetraethylammonium chloride: 2.0 g
N-octanoyl-N-methyl-glucamide: 2.1 g
polyvinylpyrrolidone (MW 25000): 3.5 g
Transpafill (sodium aluminium silicate): 62.1 g
polyvinylpropionate dispersion (50% by weight in water): 60.8 g
Bis-(2-hydroxyethyl)-(4-hydroximinocyclohexa-2,5-dienylidine)-ammonium chloride: 1.2 g
2,18-phosphomolybdic acid hexasodium salt: 16.1 g
pyrroloquinoline-quinone: 32 mg
glucose dehydrogenase rec. from Acinetobacter calcoaceticus: 1.7 MU (EC 1.1.99.17): (2.4 g)
1-hexanol: 1.6 g
1-methoxy-2-propanol: 20.4 g The total composition is adjusted with sodium hydroxide solution to a pH of ca. 6 and then coated on a 125 μm thick polycarbonate foil at a weight per unit area of 89 g/m² and dried.

The following components are added together in a beaker as pure substances or in the form of stock solutions in the following compositions and mixed by stirring:

Water: 579.7 g
sodium N-methyl-N-oleoyl-taurate 0.29 g
sodium hydroxide: 3.4 g
Gantrez (methyl vinyl ether maleic acid copolymer): 13.8 g
N-octanoyl-N-methyl-glucamide: 3.6 g
tetraethylammonium chloride: 9.7 g
polyvinylpyrrolidone (MW 25000): 20.2 g
titanium dioxide: 177.1 g
kieselguhr: 55.3 g
polyvinylpropionate dispersion (50% weight in water): 70.6 g
2,18-phosphomolybdic acid hexasodium salt: 44.3 g
potassium hexacyanoferrate (III): 0.3 g
1-hexanol: 1.6 g
1-methoxy-2-propanol: 20.4 g The total composition is adjusted with NaOH to a pH of ca. 6 and then coated as the second layer on the coated polycarbonate foil as described under A. at a weight per unit area of 104 g/m² and dried. B.4) The foil side of a 5 mm wide strip of the detection layer prepared in this manner is glued and fitted accurately on the support layer on the punched double-sided adhesive tape.

Double-sided adhesive tapes are glued as spacers onto the carrier foil directly adjacent to and on both sides of the detection layer. In the present example one spacer is 6 mm and the other is 9 mm wide. Afterwards the protective foil of the two double-sided adhesive tapes is pulled off.

A 20 mm wide strip of the spreading fleece prepared in section A is placed on this combination and is glued by pressing.

Two single-sided adhesive tapes are glued as covers onto the spreading fleece in such a manner that the spacers are completely covered and there is at least a slight overlap with the reaction zone. The tapeware is thus finished.

The tapeware is cut into 6 mm wide test carriers such that the measuring hole lies in the middle of the test carrier.

EXAMPLE 3

The production of test strips according to example 2 is repeated with the difference that the addition of 0.29 g sodium N-methyl-N-oleoyl-taurate was omitted.

Significant differences between the coating compositions of examples 2 and 3 were already apparent during knife coating on the polycarbonate base foil. A defect-free and substantially smoother coating was achieved with the compositions of example 2 compared to the compositions of example 3.

In addition the use of compositions of example 2 enabled an almost flawless initial coating to be manufactured even without plasma pretreatment of the polycarbonate foil.

EXAMPLE 4

Effect of the wetting agent additive according to the invention on the precision of functional layers of test strips manufactured according to example 2.

The glucose content was determined in whole blood at four different predetermined glucose concentrations using inventive test strips prepared according to example 2 and conventional test strips prepared according to example 3 and using ®GLUCCTREND instruments. It turned out that the reaction rate and the colour depth (% remission) was not influenced by the addition of the wetting agent according to the invention. For each glucose concentration and for each variant without and with Geropon T77, 10 measurement series each with 10 individual measurements (n=10, N=100) were carried out. From this 10 CV values were calculated for each glucose concentration and the variants without and with Geropon T77 whose medians are shown in table 2. (The CV value is defined as the relative standard deviation CV=standard deviation/mean and is stated in %).

TABLE 2

Precision of glucose coatings without and with 0.03% by weight Geropon in the wet coating composition.

| Glucose concentration [mg/dl] | CV without Gerpon [%] | CV with Geropon [%] |
|---|---|---|
| 50 | 4.1 | 3.2 |
| 100 | 2.3 | 2.3 |
| 200 | 3.0 | 2.4 |
| 400 | 3.4 | 3.0 |

The table shows that the medians of the CV values are on average 0.5% (absolute) lower when using test strips according to the invention prepared according to example 2 than when using conventional test strips prepared according to example 3. This corresponds to an average improvement of the reliability of the measured results of 18% which is due to the improved precision of the functional layers of the test strips resulting from the inventive addition of sodium N-methyl-N-oleoyl-taurate.

What is claimed is:

1. A high precision, skeleton-free functional layer comprising a film, the film comprising a film-forming polymer and reagents for the qualitative detection or quantitative determination of analytes, wherein the layer comprises a wetting agent compound of Formulas I, II and/or III:

  (I)
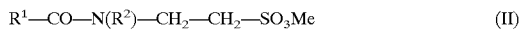  (II)
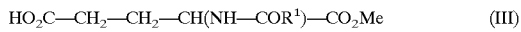  (III)

in which $R^1$ is an aliphatic residue comprising 9 to 23 carbon atoms and is either saturated or has one to three double bonds;

$R^2$ is an alkyl residue comprising 1 to 8 carbon atoms; and

Me represents hydrogen or a metal atom.

2. The skeleton-free functional layer of claim 1, wherein $R^1$ comprises an aliphatic chain of lauric acid, myristic acid, palmitic acid, stearic acid, palmitoleic acid, oleic acid, linoleic acid, linolenic acid or isomers thereof and $R^2$ is a methyl or ethyl group.

3. The skeleton-free functional layer of claim 1 wherein $R^1$ represents a quantity of alkyl residues in which the structure and proportion in the mixture of the individual alkyl residues corresponds to their structure and abundance in natural fats.

4. The skeleton-free functional layer of claim 1 wherein $R^1$—CO in Formulas I and II and $COR^1$ in Formula III is an oleoyl, cocoyl or tallow fatty acid residue and $R^2$ is methyl.

5. The skeleton-free functional layer of claim 1 wherein the compounds of Formulas I, II and III are water-soluble.

6. The skeleton-free functional layer of claim 1 wherein Me denotes an alkali metal.

7. The skeleton-free functional layer of claim 1 wherein the wetting agent compound comprises a mixture of compounds of Formulas I, II and/or III.

8. The skeleton-free functional layer of claim 1 wherein the layer comprises a total of 0.0075 to 2.5% by weight of the wetting agent compound.

9. The skeleton-free functional layer of claim 1 wherein the layer additionally comprises auxiliary substances and/or additives for the qualitative detection or quantitative determination of analytes.

10. A test strip comprising a flexible flat-shaped carrier on which at least one test field is arranged in a test region wherein each test field comprises at least one functional layer wherein at least one of the functional layers of the test strip comprises a high precision, skeleton-free functional layer comprising a film, the film comprising a film-forming polymer and reagents for the qualitative detection or quantitative determination of analytes, wherein the layer comprises a wetting agent compound of Formulas I, II and/or III:

  (I)
  (II)
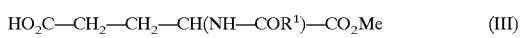  (III)

in which $R^1$ is an aliphatic residue comprising 9 to 23 carbon atoms and is either saturated or has one to three double bonds;

$R^2$ is an alkyl residue comprising 1 to 8 carbon atoms; and

Me represents hydrogen or a metal atom.

11. The test strip of claim 10 wherein each test field comprises a transparent foil and mounted thereon a first and a second functional layer lying on top of each other, wherein the first layer located on the transparent foil scatters light considerably less in a wet state than the overlying second layer and wherein the side of the foil which is opposite to that side of the foil on which the first layer is applied is the detection side and the side of the second layer which is opposite to the side of the second layer which rests on the first layer is the sample application side.

12. The test strip of claim 11 wherein the combined thickness of the first and second functional layers in the dry state is no greater than 0.20 mm.

13. The test strip of claim 10 wherein the carrier comprises a hole over which a detection layer comprising a plurality of adjacent reaction zones is located.

* * * * *